US005811240A

United States Patent [19]

Ferreira et al.

[11] Patent Number: 5,811,240

[45] Date of Patent: Sep. 22, 1998

[54] **SPECIES-SPECIFIC MITOCHONDRIAL SEQUENCES FOR IDENTIFICATION OF *TILLETIA INDICA*, THE KARNAL BUNT WHEAT FUNGUS AND METHODS OF USING SAID SEQUENCES**

[75] Inventors: Marisa A. S. V. Ferreira, Brasileia, Brazil; Paul W. Tooley; Efstathios Hatziloukas, both of Frederick, Md.; Norman W. Schaad, Myersville; Morris R. Bonde, Middletown, both of Md.

[73] Assignee: The United States of America as represented by the Secretary of Agriculture, Washington, D.C.

[21] Appl. No.: 773,739

[22] Filed: Dec. 24, 1996

Related U.S. Application Data

[60] Provisional application No. 60/009,437 Dec. 29, 1995.

[51] Int. Cl. [6] .......................... C07H 21/04; C12Q 1/68; C12P 19/34

[52] U.S. Cl. .......................... 435/6; 435/91.2; 536/23.1; 536/24.32; 536/24.33; 935/8; 935/78

[58] Field of Search .................... 435/6, 91.2; 536/23.1, 536/24.32, 24.33; 935/8.78

[56] References Cited

PUBLICATIONS

Forster et al. Experimental Mycology. 14:18–31, 1990.

*Primary Examiner*—Carla J. Myers
*Attorney, Agent, or Firm*—M. Howard Silverstein; Randall E. Deck; John D. Fado

[57] ABSTRACT

Mitochondrial DNA of five isolates of *Tilletia indica* was isolated and digested with several restriction enzymes. A 2.3 kb- EcoRI fragment was chosen, cloned, and shown to hybridize with total DNA restricted with EcoRI from *T. indica* and not from a morphologically similar smut fungus, *T. barclayana.* The clone was partially sequenced, primers were designed and tested under high-stringency conditions in PCR assays. The primer pair Ti1/Ti4 amplified a 2.3 kb fragment from total DNA of 17 *T. indica* isolates from India, Pakistan and Mexico. DNA from 25 isolates of other smut fungi (*T. barclayana, T. foetida, T. caries, T. fusca* and *T. controversa*) did not produce any bands as detected by ethidium bromide-stained agarose gels and Southern hybridizations. Sensitivity of the assay was determined and increased by using a single nested primer in a second round of amplification, so that 1 pg of total mycelial DNA could be detected. The results indicated that the primers which originated from a cloned mtDNA sequence can be used to differentiate *T. indica* from other Tilletia species and have the potential to identify teliospores contaminating wheat seeds.

17 Claims, No Drawings

SPECIES-SPECIFIC MITOCHONDRIAL SEQUENCES FOR IDENTIFICATION OF *TILLETIA INDICA*, THE KARNAL BUNT WHEAT FUNGUS AND METHODS OF USING SAID SEQUENCES

CROSS REFERENCE TO RELATED APPLICATIONS

This application hereby claims the benefit of U.S. provisional patent application Ser. No. 60/009,437, filed Dec. 29, 1995, the contents of which are incorporated by reference herein.

BACKGROUND OF THE INVENTION

1. Field of the Invention

The invention relates to novel oligonucleotide sequences which may be used as primers for the identification of *Tilletia indica* by polymerase chain reaction (PCR) assays.

2. Description of the Prior Art

The basidiomycete fungus *Tilletia indica* Mitra [syn. Neovossia indica (Mitra) Mundkur] causes Karnal bunt of wheat, an economically important disease in several countries including India, Mexico, Pakistan, Nepal, Iraq and Afghanistan (39,43). The pathogen reduces weight and viability of the seeds and also affects quality of the flour (40). Due to its seed and soil-borne nature and lack of an effective method for chemical control (44), the disease is regarded of quarantine significance. Wheat movement into Karnal bunt-free countries is strictly regulated (4, 43). The detection of Karnal bunt is based primarily on the presence of teliospores on wheat seeds. However, accurate and reliable identification of *T. indica* teliospores is not always possible using spore morphology alone. The morphologically similar teliospores of the widely distributed rice kernel smut fungus, *T. barclayana* (Bref.) Sacc. & Syd., can be found as contaminants on harvested or stored wheat and misidentified as *T. indica* (4). Therefore, a reliable and specific method is needed for accurate identification of the Karnal bunt pathogen.

Molecular methods based on DNA analysis have provided very useful information for species identification of important plant pathogens (9, 29, 49). Polymerase chain reaction (PCR) is a powerful tool that has made a significant contribution to plant disease diagnosis (21), including the detection and identification of regulated seed-borne pathogens (17, 30, 36) and obligate parasites that cannot be grown in culture (24, 47). Several different approaches have been used to develop species-specific PCR primers for fungal plant pathogens. These include cloning of genomic DNA (12), use of mitochondrial DNA (mtDNA) (19), use of random amplified polymorphic DNA sequences (47), and analysis of conserved and spacer regions of the nuclear (33, 34, 42) and mitochondrial ribosomal RNA gene (26). Fungal mitochondrial DNA has been used widely as a source of molecular markers for evolution (5), taxonomy (29) and genetic diversity studies (13). The relatively small size of the mitochondrial genome (5, 46) and the existence of conserved and variable regions makes it suitable for assessment of genetic variation, allowing the differentiation of closely related species (26, 32). High copy number, associated with mtDNA, also makes it a suitable target for DNA amplification by PCR (20). MtDNA clones have been useful for isolate and species identification (20, 28). Due to its smaller size, cloning of mtDNA may be less time-consuming for identification of specific sequences than screening of random clones of genomic DNA (28), an approach used with other fungal pathogens (12, 27, 48).

SUMMARY OF THE INVENTION

We have now discovered novel oligonucleotide primers for distinguishing *Tilletia indica* from *T. barclayana* by polymerase chain reaction (PCR) (14). These primers specifically amplify DNA fragments unique to *T. indica;* the DNA fragments are not amplified from any other Tilletia species. The presence of *T. indica* in biological samples, particularly grains such as wheat, may be detected by PCR using the disclosed primers. The primers may also be incorporated into kits for the detection and identification of *T. indica*.

In accordance with this discovery, it is an object of this invention to provide novel oligonucleotides as primers for PCR assays for the specific detection and identification of *T. indica*.

It is also an object of this invention to provide PCR assay methods using the primers for the detection and identification of *T. indica*.

Other objects and advantages of this invention will become readily apparent from the ensuing description.

DETAILED DESCRIPTION OF THE INVENTION

The oligonucleotide primers of this invention were developed by sequence analysis of a cloned 2.3 kb EcoRI fragment of mitochondrial DNA of *Tilletia indica*. The primers have been designated Ti1 and Ti4, and have the following DNA sequences: 5'TGG GCT GAG TCT GAG ATG C3', (SEQ ID NO: 2) and 5'AGT AAT ACC TGC GTC TCA TAG C3', (SEQ ID NO: 1) respectively. Primers Ti1 and Ti4 generate an 2.3 kb amplification product from all isolates of *T. indica,* but they do not amplify DNA from other Tilletia species. The invention further relates to a third internal primer, designated Ti5, which was also developed from the above-mentioned fragment of mtDNA, and has the DNA sequence: 5'ACG TCG GAT GGC TCA TCT AC3' (SEQ ID NO: 3). As will be described in more detail hereinbelow, primer Ti5 (SEQ ID NO: 3) is preferably used in combination with primer Ti1 (SEQ ID NO: 2) in a nested PCR assay, following a first PCR reaction with primers Ti1 (SEQ ID NO: 2) and Ti4 (SEQ ID NO: 1).

When used in combination with primer Ti1, primers Ti1 and Ti5 generate a shorter 2.2 kb amplification product which is also unique to *T. indica* and is not produced from other Tilletia species.

In accordance with the preferred embodiment, optimal results have been obtained using primers which are identical in length and DNA sequence to the above described primers Ti1 (SEQ ID NO: 2), Ti4 (SEQ ID NO: 3), and/or Ti5 (SEQ ID NO: 1). However, the practitioner skilled in the art will recognize that the length of the primers used may vary. For example, it is envisioned that shorter primers containing at least 15, and preferably at least 17, consecutive bases of the nucleotide sequences of these primers (i.e. Ti1, Ti4, and/or Ti5) (SEQ ID NO: 3) may be suitable. Non-complementary nucleotide fragment may also be attached to the 5' end of the primers, effectively increasing their length. The exact upper limit of the length of the primers is not critical. However, typically the primers will be less than or equal to approximately 50 bases, preferably less than or equal to 30 bases. Further still, the bases included in the primers may be modified as is conventional in the art, including but not limited to, incorporating detectable labels such as biotin, or fluorescent labels.

Detection of *T. indica* is generally accomplished by amplifying the DNA from a test sample by polymerase chain reaction and assaying for the presence of the above-mentioned amplification products. DNA for the amplification process may be prepared by lysing the cell wall of fungi present in the collected samples, extracting, and collecting the released DNA. While it is envisioned that crude cell lysate may be used, the skilled practitioner will recognize that any non-DNA material present in the sample may interfere with the polymerase reaction or subsequent analysis. The actual method of sample preparation will also vary with the structure or stage of development of the target fungi. For instance, without being limited thereto, when assaying samples of teliospores, the spores are preferably crushed and lysed, such as by grinding and suspension in cell lysis buffer, followed by digestion with proteinase and RNase. When assaying samples of mycelia, the cell wall is preferably lysed such as by freezing and grinding, and the DNA extracted using conventional techniques. Alternatively, a direct PCR could be used without extracting DNA, such as a hot start protocol recognized in the art.

Prior to cell lysis and DNA extraction, the sample of microorganisms may be subjected to an optional preliminary step of culturing (biological amplification) in order to expand the number of microorganisms. Although the PCR assay is sufficiently sensitive that such a preliminary step is not essential, as a practical matter, reliability is enhanced and sensitivity is increased when very low numbers of microorganisms are assayed. Preliminary culture of the sample is preferably employed when assaying samples containing less than about 1,000 teliospores, particularly those containing less 10 teliospores, and a nested PCR is not used. Culture may be conducted using techniques conventional in the art, including but not limited to culture in potato dextrose broth. The nested PCR assay using primers Ti1 (SEQ ID NO: 2) and Ti5 (SEQ ID NO: 3) as described hereinbelow, provides substantially greater sensitivity than PCR using the single set of external primers Ti1 (SEQ ID NO: 2) and Ti4 (SEQ ID NO: 1), thereby rendering a preliminary culture step expendable even for samples containing low numbers of microorganisms.

Amplification is carried out according to conventional procedures in the art, such as described by Mullis (U.S. Pat. No. 4,683,202), the contents of which are incorporated by reference herein. Generally, PCR is conducted in a reaction mixture comprising a suitable buffer, such as 10 mM Tris-HCl, pH 8.3, 50 mM KCl, 1.5 mM $M_2Cl_2$, 0.001% wt/vol gelatin. The reaction mixture also comprises the template DNA, the DNA polymerase, a pair of primers (e.g., Ti1 and T14), and an ample amount of each of the four deoxynucleoside triphosphates (dATP, dCTP, dGTP, and TTP). The amount of polymerase must be sufficient to promote DNA synthesis throughout the predetermined number of amplification cycles. Guidelines as to the actual amount of polymerase are generally provided by the supplier of the PCR reagents and are otherwise readily determinable by a person of ordinary skill in the art. The amount of each primer must be in substantial excess of the amount of target DNA to be amplified. The amount of primer needed for the reaction mixture can be estimated in terms of the ultimate number of amplified fragments desired at the conclusion of the reaction.

To prevent false positive or negative results, the skilled practitioner will recognize that the assays should include controls as is conventional in the art. For instance, suitable negative controls may contain no primer or no DNA (i.e. "water controls"), as well as DNA from a closely related microorganism such as T. barclayana. Positive controls may contain DNA from known T. indica samples. Positive control assays are also preferably conducted using suitable universal PCR primers, such as ITS3 and ITS4 described by White et al., [1990, Amplification and direct sequencing of fungal ribosomal RNA genes for phylogenetics, In: Innis et al., (Eds.), PCR Protocols, Academic Press, San Diego, pp. 315–322] and Smith et al. (1996, Phytopathology, 86:115–122), the contents of each of which are incorporated by reference herein.

The reaction mixture is preferably overlaid with a mineral oil or the like for the purpose of preventing evaporation of the medium and undesired increases in the concentrations of the reagents during the course of the reaction. The first step of the reaction involves heating the mixture to melt the DNA; that is, to denature double-stranded configuration to two single-stranded templates. Using as an example Taq polymerase, the denaturing is typically conducted at a temperature in the range of about 90°–96° C. for about 1–2 min. The second step of the cycle is a cooling to about 35°–65° C., and preferably 50°–60° C., for about 1–3 min to permit annealing of the primers to the template. In the third step, the mixture is held within the temperature range of about 70°–75° C. for about 2–4 min to allow for primer extension by the polymerase. This cycle is usually repeated approximately 20–30 times in order to achieve the desired amplification of the target sequence. Eventually amplification reaches a plateau as the proportion of reagents to products diminishes. In general, it is recognized that continuing amplification significantly beyond 30 cycles may introduce abnormalities. Of course it is understood that the conditions set forth herein are merely exemplary, and optimization of the conditions for any given PCR would be within the purview of the person in the art. Additional detail regarding PCR is given by Arnhelm et al. [C&EN, pages 36–47 (Oct. 1, 1990)], herein incorporated by reference.

At the conclusion of the amplification reaction, the 2.3 kb amplified product may be detected using techniques conventional in the art. In the preferred embodiment, the amplification products are conveniently visualized by gel electrophoresis and ethidium bromide staining in comparison with preestablished standards. Alternative techniques for the detection of the amplification products include Southern or dot-blot hybridization techniques utilizing DNA sequences internal to the oligonucleotide primers. The primers of this invention are also suitable for use in conventional labeled assay systems, including but not limited to the TAQMAN assay, when used in combination with a labeled probe which is internal to the primers, as described by Livak et al. (U.S. Pat. No. 5,538,848), the contents of which are incorporated by reference herein.

In an alternative, preferred embodiment, following completion of the amplification reaction with primers Ti1, (SEQ ID NO: 2) and Ti4 (SEQ ID NO: 1), a second cycle of amplification is commenced using primers Ti1 and Ti5 (SEQ ID NO: 3) in a nested PCR reaction.

Again, the nested PCR may be practiced using techniques which are well-known in the art, such as described by Myers et al. (1988, Detection of single base changes in DNA: ribonuclease cleavage and denaturing gradient gel electrophoresis, In Genome Analysis a Practical Approach, K Davies (ed.), IRL Press, Washington, D.C., pages 95–139) or Mullis et al. (1986, Cold Spring Harbor Symp. Quant. Biol., 51:263), the contents of each of which are incorporated by reference herein. Briefly, after the first round of amplification reactions with primers Ti1 (SEQ ID NO: 2) and Ti4 (SEQ ID NO: 1), a small amount of the 2.3 kb product is recovered and used as a template for a second round of PCR with primers Ti1 and Ti5 (SEQ ID NO: 3).

The conditions and number of cycles in this second round of amplification may be selected as before.

Because primer Ti5 hybridizes at an internal position within the first 2.3 kb amplified product, this nested amplification reaction generates a shorter 2.2 kb product. The 2.2 kb product may then be detected using the same procedures described hereinabove. This nested procedure provides greatly increased sensitivity, allowing the detection of significantly lower amounts of T. indica DNA.

The oligonucleotide primers of this invention may be prepared using any conventional DNA synthesis method, such as, phosphotriester methods such as described by Narang et al. (1979, Meth. Enzymol., 68:90) or Itakura (U.S. Pat. No. 4,356,270), or and phosphodiester methods such as described by Brown et al. (1979, Meth. Enzymol., 68:109), or automated embodiments thereof, as described by Mullis et al. (U.S. Pat. No. 4,683,202). In one such automated embodiment diethylphosphoramidites are used as starting materials and may be synthesized as described by Beaucage et al., Tetrahedron Letters (1981), 22:1859–1862. One method for synthesizing oligonucleotides on a modified solid support is described in U.S. Pat. No. 4,458,066, the contents of which are incorporated by reference herein. It is also possible to use a primer which has been isolated from a biological source (such as a restriction endonuclease digest).

The oligonucleotide primers may be used to detect T. indica obtained from virtually any source. However, in the preferred embodiment, the primers are particularly advantageous for the detection of T. indica on grains, most particularly wheat. Fungal samples may be collected using techniques known in the art, such as washing followed by filtration or centrifugation, brushing, or scraping. Using a single round of PCR amplification with one pair of the primers, T. indica DNA can be reliably detected at a level of 500 pg. However, when all primers are used in a nested PCR, T. Indica DNA may be reliably detected at a level as low as 1 pg.

As mentioned hereinabove, the primers may be incorporated into a convenient kit for detecting T. indica. The kit should contain at least one pair of Ti1 (SEQ ID NO: 2) and Ti4 (SEQ ID NO: 1), or Ti1 and Ti5 (SEQ ID NO: 3), although all primers may be included for added flexibility and reliability, particularly when use of nested PCR is envisioned.

The following examples are intended only to further illustrate the invention and are not intended to limit the scope of the invention which is defined by the claims.

EXAMPLES

The primers and assay disclosed hereinbelow are described by Ferreira et al. [1996, Applied and Environmental Microbiology, 62(1):87–93] the contents of which are incorporated by reference herein.

Materials and Methods

Isolates and growth conditions. A list of the isolates used in this study is given in Table 1. The isolates were originated from infected seed samples and the sources are indicated when possible. The identity of the isolates had been previously determined in our lab or by other workers based on morphology, symptomatology and/or pathogenicity tests. Mycelial cultures were grown on potato dextrose agar (PDA) for 7–10 days at 20° C. Secondary sporidial cultures were produced by adding sterile distilled water to a PDA culture and using the resulting suspension to inoculate water-agar plates. After 3–4 days of incubation at 20° C., several agar plugs were taken from the secondary sporidial cultures and placed into a 1000 ml-flask containing YM broth (DIFCO, Detroit, Mich.). Liquid cultures were kept at 20°–24° C. on a shaker at 150 rpm. After 5–7 days, mycelia were harvested by filtration through Miracloth (Calbiochem Corp., La Jolla Calif.), lyophilized, and stored at −20° C. until use.

Genomic and mitochondrial DNA extractions. Total DNA of Tilletia isolates was extracted from 0.5–2 g of lyophilized mycelia using the procedure described by Crowhurst et al. (10) except that the nucleic acid pellets were resuspended in 4 ml TE (10 mM Tris, 1 mM EDTA, pH 8.0) after precipitation with isopropanol. In the final step, DNA was resuspended in 7 ml of TE buffer. Mitochondrial DNA (mtDNA) was isolated from five isolates each of T. indica and T. barclayana using a modified procedure of Karlovsky & de Cock (22). Total DNA (300–500 µg) was subjected to cesium chloride density gradient centrifugation with bisbenzamide (Hoeschst 33258, Sigma). Cesium chloride (7.7 g) was added to the DNA solution (7 ml) and gently mixed until dissolved. Bisbenzimide (70 µl) was added from a stock solution of 10 mg/ml. The gradients were centrifuged at 55,000 rpm for 22–24 hours in a Beckman Ti 70.1 rotor, at 20° C. Bisbenzimide was removed from DNA samples with isopropanol saturated with 20XSSC (1 X SSC is 0.15M NaCl; 0.015M trisodium citrate) and the mtDNA solution was diluted with 3 volumes of TE buffer, ethanol precipitated and the final pellet resuspended in 200 µl of TE buffer. All DNA quantifications were based on electrophoretic separation with ethidium bromide staining on 0.7% agarose gels using phage λ-HindIII fragments as a standard. DNA samples were stored at −80° C. until use.

Restriction digestion and cloning of mtDNA. Restriction enzymes were obtained from GIBCO-BRL (Bethesda Research Laboratories, Gaithersburg, Md.) and all digestions were performed according to the manufacturer's recommendations. DNA fragments were electrophoresed in 0.7 % agarose gels in 0.5X Tris-borate-EDTA (0.045M Trisborate; 0.001M EDTA). DNA was visualized after staining with ethidium bromide (0.5 µg/ml). Gels were photographed under short wave UV using Polaroid type 57 film.

Mitochondrial DNA obtained from T. indica and T. barclayana isolates was digested with a number of restriction endonucleases. Selected restriction fragments to be cloned were eluted from agarose gels using the Glass Max DNA isolation spin cartridge system (GIBCO-BRL, Gaithersburg, Md.) and ligated into the plasmid vector PGEM 7zf(+) (Promega, Madison, Wis.) by standard cloning procedures (35). The product of the ligation reaction was used to transform E. coli DH5α competent cells (Subcloning efficiency DH5α competent cells, GIBCO-BRL). Recombinant clones were identified and the presence of inserts was confirmed by a PCR procedure using the primers for the SP6 and T7 promoters of the plasmid vector and 1 µl of the bacterial culture. Recombinant clones also were obtained by shotgun cloning. Purified mtDNA of one isolate of T. indica (A4S2) was restricted with EcoRI and, after a phenol/chloroform extraction and ethanol precipitation (35), the various fragments were ligated into pGEM7zf(+).

Southern and dot blot hybridizations. Plasmid DNA was extracted by the boiling method (35) and labeled in vitro by random priming 25 ng of plasmid DNA with [α-$^{32}$P]dCTP ("Ready-to-go kit", Pharmacia, Piscataway, N.J.). Total DNA (0.7 µg) extracted from several isolates of T. indica and T. barclayana were restricted with EcoRI at 37° C. and fragments were electrophoresed in 0.7% agarose gels. DNA fragments were denatured and blotted onto Nytran (Micron Separations Inc., Westboro, Mass.) nylon membranes by capillary transfer for 16 hr. Pre-hybridization was carried out at 65° C. for one hour in 0.25M NaHPO$_4$, pH 7.2, 0.25M NaCl, 7% SDS, 1 mM EDTA (1). Hybridization was performed at the same temperature for 14–16 hr, after the addition of 200 μl (1.4×10$^8$ cpm) of the radiolabeled probe. Filters were washed at 65° C. for 20 min in 2 X SSC, 0.1% SDS and twice in a 0.1 X SSC, 0.1% SDS solution. Membranes were exposed to X-ray film (Hyperfilm MP, Amersham) and placed between intensifying screens (Lightning Plus) at –80° C. for 24–72 hours. For the dot blot hybridization, bacterial cultures were grown overnight in LB broth at 37° C. and 1 μl of the culture was used in a PCR assay with primers SP6 and T7. One μl of the PCR product was denatured with one volume of 0.4N NaOH and applied to a nylon membrane. Two replicates were prepared. Pre-hybridization, hybridization and membrane washes were performed as described above.

Sequencing and primer design. The clone pTi23, which contains a 2.3 kb-EcoRI insert from the mtDNA of *T. indica* isolate A1S4, was partially sequenced. A Sequenase kit (Sequenase version 2.0, US Biochemical, Cleveland, Ohio) was employed for sequencing reactions. Reaction products were electrophoresed on 6% polyacrylamide gels that were dried, and subjected to autoradiography. Sequences were analyzed using the GCG program (11, 16). Candidate primers were identified using the program PRIMER version 0.5 (MIT Center for Genome Research & Whitehead Institute for Biochemical Research, Cambridge, Mass.). Four pairs of primers were designed for PCR amplification of the target fragment using the following criteria: a 19–23 bp length, melting temperature (Tm) between 55° and 65° C. and a GC content between 40 and 60%. The primers were synthesized commercially by Macromolecular Resources (Fort Collins, Colo.).

PCR conditions. Primers were screened for specificity to *T. indica* in 25μl reactions containing 10–20 ng genomic DNA, 100 μM each of dNTPs, 12.5 pmol of each primer, 1X PCR buffer (10 mM Tris HCl, pH 8.3, 50 mM KCl, 1.5 mM MgCl$_2$, 0.001% gelatin) and 0.5 U AmpliTaq DNA polymerase (Perkin Elmer). All experiments were conducted in a Perkin Elmer 9600 thermocycler (Gene Amp PCR System 9600, Perkin Elmer Cetus, Norwalk, Conn.), with an initial DNA denaturation at 94° C. for 1 min followed by 30 cycles of 94° C./15 s; 65° C./15 S; 72° C./15 s and a final extension step of 6 min at 72° C. Ten μl of the reaction were electrophoresed on 0.7% agarose gels, followed by staining with ethidium bromide. The DNA products were transferred to nylon membranes and probed with $^{32}$p-labeled pTI23 that contains the 2.3 kb fragment, following the same procedure described above.

Nucleotide accession numbers. The flanking sequences of the 2.3 kb mtDNA fragment have been submitted to Gen-Bank database and assigned the accession numbers U37693 and U37585.

Results

MtDNA restriction analysis and selection of a unique fragment. Cesium-chloride density gradients produced three visible bands for both *T. indica* and *T. barclayana*, corresponding to the mitochondrial, nuclear and, possibly, ribosomal DNA, as observed in other fungal species (15). Restriction digests of the upper gradient band (mtDNA), revealed a pattern of distinct bands while the lower band, corresponding to the nuclear fraction, showed a smear of digested DNA (data not shown). The mtDNA of *T. indica* isolate A4S2 and *T. barclayana* isolate P-5 were initially digested with 18 restriction enzymes. The enzymes EcoRI, MspI, BclI and BglII were selected for producing fewer (10–20) and distinct fragments, smaller than 23 kb. Ten additional isolates were analyzed using EcoRI-restriction digests. Differences in banding pattern within each species and between species were detected. EcoRI-digestion patterns showed conservation of restriction sites among different isolates; however, there were restriction fragments unique to isolates A1S4 and A4S2. *T. indica* isolates showed at least six common bands when mtDNA was restricted with EcoRI and two fragments of approximate sizes 2.3 and 1.6 kb were observed in all five isolates of *T. indica* and not detected in *T. barclayana*. These fragments were selected for further cloning and hybridization experiments. Both cloned *T. indica* mtDNA fragments hybridized strongly with total restricted DNA from 5 isolates of *T. indica* after a 72 hour-exposure. Clone pTI23, that contains the 2.3 kb fragment, produced no signal for any of the five *T. barclayana* isolates. Clone pTI16, containing the 1.6 kb insert, hybridized weakly with DNA from the *T. barclayana* isolates, showing low specificity. These results were confirmed by dot blot hybridizations. Plasmid pTI23 hybridized with total labeled DNA of *T. indica* and not with combined DNA of 5 *T. barclayana* isolates.

Primer specificity. Clone pTI23 was partially sequenced, five primers were designed and used in four combinations. The best results were obtained with primers Ti-1 (SEQ ID NO:2) and Ti-4 (SEQ ID NO: 1) using the PCR conditions described in Materials and Methods. These primers amplified a product of approximately 2.3 kb in length. The other primers tested did not show specificity; amplification products were also observed in *T. barclayana*. Primers Ti-1 and Ti-4 produced a single band for *T. indica* and none for *T. barclayana* as detected on ethidium bromide-stained agarose gels. DNA from 17 isolates of *T. indica* representing field collections from different geographic areas (Table 1) were tested with primers Ti-1 and Ti-4, and a 2.3 kb product was amplified with DNA from all isolates. The specificity and identity of the product was confirmed by Southern hybridizations using labeled pTI23 as a probe. A total of 25 isolates belonging to different Tilletia species (Table 1) were tested and no detectable product was observed. Specificity of primer pair Ti-1 and Ti-4 was tested also with the genomic DNA extracted from 20 isolates representing 19 species and 13 fungal genera isolated from wheat seeds. No PCR product was detected, a result confirmed by Southern hybridization (data not shown).

Restriction digestion of PCR products. The amplification of a sequence as large as 2.3 kb allows the use of restriction endonucleases to detect differences among isolates. We investigated the degree of sequence conservation among different isolates using MspI-restriction digestion patterns of the PCR-amplified 2.3 kb sequence. The restriction sites were highly conserved among the isolates; 15 out of 17 isolates presented the same restriction pattern. Polymorphisms were detected in two isolates, Mx-4 and A4S2 (data not shown). This test also confirmed the identity of the amplified PCR product. The same banding pattern was observed for pTI23 and the 17 test isolates.

Sensitivity threshold. The detection limit of the PCR amplification of the *T. indica*-specific 2.3 kb mtDNA sequence was evaluated by using serial dilutions of purified total mycelial DNA of *T. indica* A1S4. Initially, the primer pair Ti-1 (SEQ ID NO:2)/Ti-4. was used in a single round of amplification. The detection limit was 500 pg of total DNA, using a longer extension step (72° C./60 sec) and 30 cycles of amplification. In order to improve sensitivity, a hemi-nested assay, one which uses one external and one internal primer, was employed. A nested primer, Ti-5 (SEQ ID NO: 3) and external primer Ti-1, (SEQ ID NO: 2) were used after a 1:50 dilution of the products obtained from the first PCR run. The sensitivity was improved 500 fold, so that 1 pg of DNA was amplified and the product detected by ethidium-bromide staining, without the need for probing to detect the products. The *T. indica*-specific 2.2 kb product obtained with primer pair Ti-1/Ti-5 was only detected with *T. indica* isolates; however, several secondary smaller products were detected in 11 of 18 isolates of *T. barclayana*. Southern hybridization showed that those bands had no homology with the originally cloned mtDNA fragment, although a longer exposure period revealed a weak hybridization signal of approximately the same size of the *T. indica* specific band from PCR reactions with two isolates of *T. barclayana*, P-T15 and Tsp5 and one isolate of *T. fusca* (Tsp27).

Discussion

Although *T. indica* can be identified through pathogenicity tests and isozyme analysis (4), both methods are time-consuming. Spore morphology is also important and useful in Tilletia identification but more sensitive and specific methods may help to overcome difficulties, especially in regulatory situations. PCR has been shown to be a highly sensitive and specific method for identification of a wide range of plant pathogens (12, 24, 25, 36, 42).

In this study, a *T. indica*-unique restriction fragment was cloned, sequenced and, used to design specific primers to identify the fungus in a simple and rapid PCR assay. The oligonucleotide primers described here showed specificity for *T. indica* when tested against DNA extracted from five other Tilletia species infecting wheat and other grasses. The sensitivity of the primers was assessed and we observed a 500-fold increase in the detection limit by using one internal primer and one original external primer in a second round of amplification. The sensitivity of a PCR assay depends on several factors including, the primers used (18) and the number of target sequences present in the reaction. Although the 2.3 kb fragment originated from the mitochondrial genome and it is expected to occur in multiple copies per cell, a higher sensitivity level was only obtained after the use of hemi-nested primers.

Increased sensitivity of PCR detection using nested primers has been reported (24, 36, 37). We were able to detect 1 pg of purified mycelial DNA using this approach, a sensitivity level higher than those observed with primers specific to *Stagonospora tritici* (3) or Phytophthora parasitica (12), using standard PCR methods. The increased sensitivity achieved with a hemi-nested PCR approach for *T. indica* had little effect on the specificity of the assay. The presence of a weaker band detected by Southern hybridization with the DNA from three other Tilletia isolates indicates that the sequence might be present in a lower copy number in some Tilletia spp., requiring more sensitive methods for its detection or, it might have low homology to the *T. indica* mitochondrial sequence.

A high level of diversity is commonly found in fungal mtDNA (13, 14, 23, 29, 31) and the major cause of intraspecific variation in mtDNA is attributed to insertion and deletion events (6, 29). Polymorphisms found between fungal species may involve loss of the DNA fragment or, loss of the ability to detect it through hybridization (5). We found that two morphologically and biologically similar species *T. indica* and *T. barclayana* showed very distinct mtDNA restriction digestion patterns. MtDNA restriction digestion patterns varied among *T. indica* isolates, but no distinct subgroups were found that could be correlated with the geographic origin of the isolates. Different banding patterns were observed even between a single teliospore culture and its monosporidial lines originated from the same teliospore (data not shown).

We found that the MspI-restriction patterns of the amplified 2.3 kb region were conserved among *T. indica* isolates. The differences observed in two isolates could not be correlated with the geographic origin of the isolate or the original teliospore population. The conservation of restriction sites in this region also could be used as an additional identification tool after amplification of the sequence by PCR.

A potential use of the *T. indica*-specific primers would be the direct identification of teliospores detected on wheat seeds. Amplification of DNA directly extracted from fungal hyphae and spores has been reported (19, 38, 45). Theoretically, the detection limit of PCR is estimated to be as low as one single target cell in the reaction mixture (41). Amplification of template DNA equivalent to that from one single cell of *X. campestris* pv.phaseoli (2), from a single spore of the tobacco blue mold pathogen (47) and a single boiled ascospore of *Gaeumannomyces graminis* (19) have been successfully achieved. Recently, a method for separating *T. indica* teliospores from seeds and debris was developed (7). The method can be used for extracting teliospores for later use in a PCR-based identification technique. We have attempted to extract and amplify DNA from a small number of ungerminated *T. indica* teliospores. Inhibition of the reaction was observed after adding as little as 1 μl of a crude buffer extract of crushed teliospores in a standard reaction mixture. In the future, different procedures to overcome PCR inhibition problems (20) might be explored in order to develop a method to consistently extract and amplify DNA from ungerminated teliospores. Although direct amplification from ungerminated spores was not achieved, our preliminary results show that once spores were allowed to germinate, positive PCR identification was obtained with DNA extracted from mycelia produced by one single teliospore (data not shown).

The potential risk of seed transmission of *T. indica* in international wheat shipments and worldwide exchange of germplasm is a serious concern in many Karnal bunt-free countries. Infected seeds can be visually separated from wheat seed lots, however, teliospores contaminating the surface of healthy seeds are not readily detected and can be carried to disease-free areas and establish a primary source of inoculum (8). The existence of a PCR-based method to identify *T. indica* represents a valuable tool for monitoring natural disease spread, tracking airborne sporidia in field studies and detecting the presence of teliospores on seed lots entering Karnal bunt-free areas.

It is understood that the foregoing detailed description is given merely by way of illustration and that modifications and variations may be made therein without departing from the spirit and scope of the invention.

TABLE 1

Species and isolates used in this study and results of PCR assay using *T. indica* - mtDNA -derived primers (Ti-1/Ti-4).

| Species | Isolate[a] | Host | Origin[b] | PCR amplification[c] |
|---|---|---|---|---|
| *Tilletia indica* | A1S4 | wheat | Pantanagar, India, 1991 | + |
| *T. indica* | A3S4 | wheat | Pantanagar, India, 1991 | + |
| *T. indica* | A4S2 | wheat | Pantanagar, India, 1991 | + |
| *T. indica* | B4S4 | wheat | Pakistan, 1985 | + |
| *T. indica* | D3S3 | wheat | Sonora, Mexico, 1981 | + |
| *T. indica* | Tsp1 | wheat | North India (=ATCC36194) | + |
| *T. indica* | Mx-1 | wheat | Navajoa, Mexico, 1986 | + |
| *T. indica* | Mx-2 | wheat | CIANO Station, Mexico, 1991 | + |
| *T. indica* | Mx-3 | wheat | Calexico, California, 1986 | + |
| *T. indica* | Mx-4 | wheat | Mexico, 1991 | + |
| *T. indica* | Fv-1 | wheat | Fuente Valley, Mexico, 1989 | + |
| *T. indica* | Mv-10 | wheat | Mali Valley, Mexico, 1990 | + |
| *T. indica* | 83B | wheat | CIANO Station, Mexico, 1983 | + |
| *T. indica* | TL419 | wheat | India, 1989 | + |
| *T. indica* | T02 | wheat | Pakistan, 1985 | + |
| *T. indica* | T03 | wheat | Pantanagar, India, 1991 | + |
| *T. indica* | Cx-87 | wheat | Calexico, California, 1987 | + |
| *T. barclayana* | PJ-11 | rice | China, 1991 | – |
| *T. barclayana* | PJ-14 | rice | China, 1991 | – |
| *T. barclayana* | N1 | rice | China | – |
| *T. barclayana* | C-1990 | rice | India, 1990 | – |
| *T. barclayana* | Nb91b | rice | India, 1991 | – |
| *T. barclayana* | L-201 | rice | California, 1985 | – |
| *T. barclayana* | AK-T2 | rice | Arkansas, 1996 | – |
| *T. barclayana* | AK-T3 | rice | Arkansas, 1986 | – |
| *T. barclayana* | AK-T5 | rice | Arkansas, 1986 | – |
| *T. barclayana* | AK-T7 | rice | Arkansas, 1986 | – |
| *T. barclayana* | AK-T9 | rice | Arkansas, 1986 | – |
| *T. barclayana* | P-5 | rice | Philippines, 1989 | – |
| *T. barclayana* | P-6 | rice | Philippines, 1989 | – |
| *T. barclayana* | P-T15 | rice | Philippines, 1989 | – |
| *T. barclayana* | WAT-T08 | rice | Washington State, 1985 | – |
| *T. barclayana* | AK | rice | Arkansas, 1987 | – |
| *T. barclayana* | 137aI | rice | Brazil, 1992 | – |
| *T. barclayana* | Tsp14 | rice | California, 1982 (=WSP69539) | – |
| *T. barclayana* | Tsp5 | *Paspalum distichum* | Washington State (=WSP68658) | – |
| *T. caries* | Tsp4 | wheat | Washington State (=ATCC42078) | – |
| *T. controversa* | Tsp2 | wheat | Utah (=ATCC 42079) | – |
| *T. foetida* | Tsp3 | wheat | Washington State (=ATCC42080) | – |
| *T. fusca var. fusca* | Tsp26 | *Vulpia microstachys* | Washington State, 1993 | – |
| *T. f. var. fusca* | Tsp27 | *V. octoflora* | Washington State, 1991 | – |
| *T. f. var. bromitectorum* | Tsp21 | *Bromus tectorum* | Idaho, 1992 | – |

[a]The following cultures originated from a single teliospore: TL419, TO2, T03, Cx87, P6, PT15, WAT-T08; and from a teliospore population: AK. Cultures originated from a single primary sporidium: A1S4, A3S3, A4S2, B4S4 and D3S3. All others originated from a single secondary sporidium.
[b]Isolates originated from seed samples sent to our collection at USDA/Frederick, MD and other culture collections: ATCC, American Type Culture Collection; WSP, Washington State University (L. Carris)
[c]+, presence of PCR product; –, no PCR product detected.

References

1. Amasino, R. M. 1986. Acceleration of nucleic acid hybridization rate by polyethylene glycol. Anal. Biochem.152: 304–307.

2. Audy, P., A. Laroche, G. Saindon., H. C. Huang and, R. L. Gilbertson.1994. Detection of the bean common blight bacteria *Xanthomonas campestris* pv. phaseoli and X. c. phaseoli var fuscans, using the polymerase chain reaction. Phytopathology 84:1185–1192.

3. Beck, J. J., and J. M. Ligon. 1995. Polymerase chain reaction assays for the detection of *Stagonospora nodorum* and *Septoria tritici* in wheat. Phytopathology 85:319–324.

4. Bonde, M. R, G. L. Peterson, and T. T. Matsumoto.1989. The use of isozymes to identify teliospores of *Tilletia indica*. Phytopathology 79: 596–599.

5. Bruns, T. D., T. J. White, and J. W. Taylor. 1991. Fungal molecular systematics. Annu.Rev. Ecol. Syst. 22:525–564.

6. Carter, D. A., S. A. Archer, K. W. Buck, D. S. Shaw, and Shattock, R. C. 1990.Restriction fragment length polymorphisms of mitochondrial DNA of *Phytophthora infestans*. Mycol. Res. 94 (8): 1123–1128.

7. Castro, C., N. W. Schaad, and M. R. Bonde. 1994. A technique for extracting *Tilletia indica* teliospores from contaminated wheat seeds. Seed Sci. & Technol. 22: 91–98.

8. Chahal, S. S., and S. B. Mathur. 1992.Germination of deep-frozen *Tilletia indica* and *Tilletia barclayana* teliospores. FAO Plant Prot.Bull.40:31–36.

9. Correll, J. C., D. D. Rhoads, and J. C. Guerber. 1993. Examination of mitochondrial DNA restriction fragment length polymorphisms, DNA fingerprints and randomly amplified polymorphic DNA of *Colletotrichum orbiculare*. Phytopathology 83: 1199–1204.

10. Crowhurst, R. N., B. T. Hawthorne, E. H. A. Rikkerink, and M. D. Templeton. 1991. Differentiation of

*Fusarium solani* f. sp. cucurbitae races 1 and 2 by random amplification of polymorphic DNA. Curr. Genet. 20: 391–396.

11. Devereaux, J., P. Haeberli, and O. Smithies.1984. A comprehensive set of sequence analysis programs for the vax. Nucleic Acids Res. 12:387–395.

12. Ersek, T., J. E. Schoelz, and J. T. English. 1994. PCR amplification of species-specific DNA sequences can distinguish among Phytophthora species. Appl. Environ. Microbiol. 60 (7): 2616–2621.

13. Förster, H. and M. D. Coffey. 1993. Molecular taxonomy of *Phytophthora megasperma* based on mitochondrial and nuclear DNA polymorphisms.Mycol.Res.97(9):1101–1112.

14. Förster, H., P. Oudemans and, M. D. Coffey. 1990.Mitochondrial and nuclear DNA diversity within six species of Phytophthora. Exp. Mycol. 14:18–31.

15. Garber, R. C. and O. C. Yoder. 1983. Isolation of DNA from filamentous fungi and separation into nuclear, mitochondrial, ribosomal, and plasmid components.Anal. Biochem.135:416–422.

16. Genetics Computer Group.1991. Program manual for the GCG package, version 7, April 1991, 575 Science Drive, Madison, Wis. 53711.

17. Goodwin, P. H. and S. L. Annis. 1991. Rapid identification of genetic variation and pathotype of *Leptosphaeria maculans* by random amplified polymorphic DNA assay. Appl. Environ. Microbiol. 57: 2482–2486.

18. He, Q., M. Marjamaki, H. Soini, J. Mertsola, and, M. K. Viljanen.1994. Primers are decisive for sensitivity of PCR. BioTechniques 17(1):82–86.

19. Henson, J. M.; T. Goins., W. Grey, D. E. Mathre, and M. L. Elliott.1993. Use of polymerase chain reaction to detect *Gaeumannomyces graminis* DNA in plants grown in artificially and naturally infested soil. Phytopathology 83:283–287.

20. Henson, J. M. and R. French. 1993. The polymerase chain reaction and plant disease diagnosis. Annu. Rev. Phytopathol. 31: 81–109.

21. Hintz, W. E.; M. Mohan, J. B. Anderson, and P. A. Horgen. 1985. The mitochondrial DNAs of Agaricus : heterogeneity in *A. bitorquis* and homogeneity in A. brunnescens. Curr. Gen. 9: 127–132.

22. Karlovsky, P. and A. W. A. M de Cock.1991. Buoyant density of DNA- Hoechst 33258 (bisbenzimide) complexes in CsCl gradients: Hoechst 33258 binds to single AT base pairs. Anal. Biochem. 194: 192–197.

23. Kim, D. H., R. D Martyn, and C. W. Magill. 1993.Mitochondrial DNA (mtDNA)- Relatedness among formae speciales of *Fusarium oxysporum* in the Cucurbitaceae. Phytopathology 83:91–97.

24. Lee, I. -M., D. E. Gundersen, R. W. Hammond, and R. E. Davis. 1994.Use of mycoplasmalike organism (MLO) group-specific oligonucleotide primers for nested-PCR assays to detect mixed-MLO infections in a single host plant. Phytopathology 84:559–566.

25. Leite, JR., R. P., G. V. Minsavage, U. Bonas, and R. E. Stall. 1994. Detection and identification of phytopathogenic Xanthomonas strains by amplification of DNA sequences related to the hrp genes of *Xanthomonas campestris* pv. vesicatoria. Appl. Environ. Microbiol. 60: 1068–1077.

26. Li, K. N., D. I. Rouse, and T. L. German. 1994. PCR primers that allow intrageneric differentiation of Ascomycetes and their application to Verticillium spp. Appl. Environ.Microbiol. 60:4324–4331.

27. Manicom, B. Q., M. Bar-Joseph, A. Rosner,H. Vigodsky-Haas, and J. M. Kotze.1987. Potential applications of random DNA probes and restriction fragment length polymorphisms in the taxonomy of the fusaria. Phytopathology 77: 669–672.

28. Martin, F. N. 1991. Selection of DNA probes useful for isolate identification of two Pythium spp. Phytopathology 81:742–746.

29. Martin, F. N., and H. C. Kistler. 1990. Species-specific banding patterns of restriction endonuclease-digested mitochondrial DNA from the genus Pythium. Exp. Mycol. 14: 32–46.

30. McManus, P. S., and A. L. Jones. 1995. Detection of *Erwinia amylovora* by nested PCR and PCR- dot-blot and reverse-blot hybridization. Phytopathology 85:618–623.

31. Milgroom, M. G., and S. E. Lipari. 1993. Maternal inheritance and diversity of mitochondrial DNA in the chestnut blight fungus, *Cryphonectria parasitica*. Phytopathology 83: 563–567.

32. Mills, P. R. 1994. DNA-based methods for identification and characterization. Pages 427–435 in: The identification and characterization of pest organisms. D. K. Hawksworth,ed. Wallingford: CAB International.Egham, Surrey.UK.

33. Moukhamedov, R., X. Hu, R. N. Nazar and, J. Robb. 1994. Use of polymerase chain reaction-amplified ribosomal intergenic sequences for the diagnosis of *Verticillium tricorpus*. Phytopathology 84: 256–259.

34. Nazar, R. N., X. Hu, J. Schmidt, D. Culham, and J. Robb. 1991. Potential use of PCR amplified ribososmal intergenic sequences in the detection and differentiation of verticillium wilt pathogens. Physiol. and Molec. Plant Pathol. 39: 1–11.

35. Sambrook, J. F., E. F. Fritsch, and T. Maniatis. 1989. Molecular cloning: a laboratory manual. 2nd.edn. Cold Spring Harbor Laboratory, Cold Spring Harbor, New York.

36. Schaad, N. W., S. S. Cheong, S. Tamaki, E. Hatziloukas, and N.J. Panopoulos. 1995. A combined biological and enzymatic amplification (BIO-PCR) technique to detect *Pseudomonas syringae* pv. phaseolicola in bean seed extracts. Phytopathology 85: 243–248.

37. Schesser, K., A. Luder, and J. M. Henson. 1991. Use of polymerase chain reaction to detect the take-all fungus, *Gaeumannomyces graminis* in infected wheat plants. Appl. Environ. Microbiol. 57 (2): 553–556.

38. Simon, L., M. Lalonde, and T. D. Bruns. 1992. Specific amplification of 18 S fungal ribosomal genes from vesicular-arbuscular endomycorrhizal fungi colonizing roots.Appl. Environ. Microbiol. 58: 291–295.

39. Singh, D. V., R. Agarwal, J. K. Shreshtha, B. R. Thapa, and H. J. Dubin. 1989. First report of Neovossia indica in Nepal. Plant Dis. 73:277.

40. Singh, D. V., and K. D. Srivistava.1990. Detection of Karnal bunt in wheat seed lots. Bull. Grain.Tech.,28(2) 156–164.

41. Steffan, R. J. and R. M. Atlas. 1991. Polymerase chain reaction: Applications in environmental microbiology. Annu. Rev. Microbiol. 45:137–161.

42. Tisserat, N. A., S. H. Hulbert, and K. M. Sauer.1994. Selective amplification of rDNA internal transcribed spacer regions to detect *Ophiosphaerella korrae* and *O. herpotricha*. Phytopathology 84: 478–482.

43. Warham, E. J. 1986. Karnal bunt disease of Wheat: a literature review. Trop. Pest Management 32 (3): 229–242.

44. Warham, E. J., and J. M. Prescott. 1989. Effectiveness of chemical seed treatment in controlling Karnal bunt disease of wheat. Plant Dis. 73 (7): 585–588.

45. White, T. J., T. Bruns, S. Lee, and J. Taylor. 1990. Amplification and direct sequencing of fungal ribosomal RNA genes for phylogenetics, p. 315–322 In M. A. Innis, D. H. Gelfand, J. J. Sninsky, and T. J. White (eds), PCR protocols, a guide to methods and applications. Academic Press, San Diego, Calif.

46. Taylor, J. W. 1986. Fungal evolutionary biology and mitochondrial DNA. Exp. Mycol. 10: 259–269.

47. Wiglesworth, M. D., W. C. Nesmith, C. L. Schardl, D. Li, and M. R. Siegel. 1994. Use of specific repetitive sequences in *Peronospora tabacina* for the early detection of the tobacco blue mold pathogen. Phytopathology 84:425–430.

48. Yao, C. L., C. W. Magill, R. A. Frederiksen, M. R. Bonde, Y. Wang, and P. S. Wu. 1991. Detection and identification of *Peronosclerospora sacchari* in maize by DNA hybridization. Phytopathology 81: 901–905.

---

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Tilletia indica
        ( C ) INDIVIDUAL ISOLATE: A1S4
        ( I ) ORGANELLE: Mitochondrion ( v i i ) IMMEDIATE SOURCE:
        ( B ) CLONE: clone pTi23

( x i ) SEQUENCE DESCRIPTION: SEQ ID NO:1:

AGTAATACCT GCGTCTCATA GC         2 2

( 2 ) INFORMATION FOR SEQ ID NO:2:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Tilletia indica
        ( C ) INDIVIDUAL ISOLATE: A1S4
        ( I ) ORGANELLE: Mitochondrion ( v i i ) IMMEDIATE SOURCE:
        ( B ) CLONE: clone pTi23

( x i ) SEQUENCE DESCRIPTION: SEQ ID NO:2:

TGGGCTGAGT CTGAGATGC         1 9

( 2 ) INFORMATION FOR SEQ ID NO:3:

( i ) SEQUENCE CHARACTERISTICS:

(A) LENGTH: 20 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Tilletia indica
        (C) INDIVIDUAL ISOLATE: A1S4
        (I) ORGANELLE: Mitochondrion (v i i) IMMEDIATE SOURCE:
        (B) CLONE: clone pTi23

(x i) SEQUENCE DESCRIPTION: SEQ ID N